(12) United States Patent  (10) Patent No.: US 9,012,048 B2
Knoop                     (45) Date of Patent:     Apr. 21, 2015

(54) FUEL CELL SYSTEM WITH ULTRASONIC DETECTOR

(75) Inventor: Andreas Knoop, Esslingen (DE)

(73) Assignee: Daimler AG, Stuttgart (DE)

( * ) Notice: Subject to any disclaimer, the term of this patent is extended or adjusted under 35 U.S.C. 154(b) by 1385 days.

(21) Appl. No.: 12/524,538

(22) PCT Filed: Jan. 16, 2008

(86) PCT No.: PCT/EP2008/000283
§ 371 (c)(1),
(2), (4) Date: Jul. 24, 2009

(87) PCT Pub. No.: WO2008/089903
PCT Pub. Date: Jul. 31, 2008

(65) Prior Publication Data
US 2010/0028722 A1    Feb. 4, 2010

(30) Foreign Application Priority Data
Jan. 26, 2007  (DE) .................. 10 2007 003 938

(51) Int. Cl.
*H01M 14/00* (2006.01)
*H01M 8/04* (2006.01)
*G01N 29/024* (2006.01)
*H01M 8/24* (2006.01)
*H01M 8/10* (2006.01)

(52) U.S. Cl.
CPC ......... *H01M 8/04119* (2013.01); *G01N 29/024* (2013.01); *G01N 2291/02836* (2013.01); *G01N 2291/02845* (2013.01); *G01N 2291/02881* (2013.01); *H01M 8/04328* (2013.01); *H01M 8/04335* (2013.01); *H01M 8/04507* (2013.01); *H01M 8/04835* (2013.01); *H01M 8/04992* (2013.01); *H01M 8/2465* (2013.01); *H01M 2008/1095* (2013.01); *Y02E 60/50* (2013.01)

(58) Field of Classification Search
None
See application file for complete search history.

(56) References Cited

U.S. PATENT DOCUMENTS 6,568,270 B2 *  5/2003  Hongerholt .................. 73/596
2002/0110713 A1  8/2002  Reindl et al.
2003/0157392 A1  8/2003  Zhang et al.

(Continued)

FOREIGN PATENT DOCUMENTS

DE    196 53 901 A1    12/1996
DE    199 44 047 A1     9/1999

(Continued)

OTHER PUBLICATIONS

Machine translation of JP 2002-277449, Yonemura Masao, Sep. 25, 2002.*

(Continued)

*Primary Examiner* — Patrick Ryan
*Assistant Examiner* — Jose Colucci Rios
(74) *Attorney, Agent, or Firm* — Crowell & Moring LLP

(57) ABSTRACT

The invention relates to a fuel cell system, having at least one channel system (2) for a working fluid and having a device (12, 22) for adjusting the moisture content of the working fluid flowing in one direction (23) in the channel system (2), the device (12, 22) containing a sensor which represents the actual humidity in the channel system (2). The object of the invention is to develop a fuel cell system which allows reliable and dynamic measurement of the actual humidity. The invention consists in providing an ultrasonic detector (16, 17) for measuring actual humidity.

11 Claims, 3 Drawing Sheets

(56) References Cited

U.S. PATENT DOCUMENTS

| | | | |
|---|---|---|---|
| 2003/0219638 A1* | 11/2003 | Tanaka et al. | 429/26 |
| 2004/0038102 A1 | 2/2004 | Beckmann et al. | |
| 2005/0008910 A1 | 1/2005 | Lee | |
| 2005/0214603 A1 | 9/2005 | Barton et al. | |
| 2007/0281853 A1* | 12/2007 | Lee et al. | 502/101 |

FOREIGN PATENT DOCUMENTS

| | | | |
|---|---|---|---|
| DE | 100 47 248 A1 | 9/2000 | |
| DE | 101 43 841 A1 | 9/2001 | |
| DE | 101 49 333 A1 | 10/2001 | |
| EP | 1 722 433 A1 | 11/2006 | |
| GB | 2 257 255 A | 1/1993 | |
| JP | 6-68890 A | 3/1994 | |
| JP | 9-320626 A | 12/1997 | |
| JP | 2000-121616 A | 4/2000 | |
| JP | 2000-241399 A | 9/2000 | |
| JP | 2002-277449 A | 9/2002 | |
| JP | 2003-243007 A | 8/2003 | |
| JP | 2004-146236 A | 5/2004 | |
| JP | 2005-285396 A | 10/2005 | |
| JP | 2006071426 A | 3/2006 | |
| JP | 2007-128758 A | 5/2007 | |
| WO | WO 2006/024933 | * | 3/2006 |

OTHER PUBLICATIONS

Machine translation of JP 2007-128758, Tanabe et al., May 24, 2007.*

Nishikawa et al., Measurements of humidity and current distribution in a PEFC, Jul. 11, 2005, Journal of Power Sources, 155 (2006), 213-218.*

Yonemura, Masao, Fluid Dryness Measuring Device, JP2000121616, Apr. 28, 2000.*

Yonemura, Masao, Measuring Apparatus for Degree of Dryness or Wetness of Two Phase Fluid, JP2002277449, Sep. 25, 2002.*

Nishikawa et al., Measuring of Humidity and Current Distribution in a PEFC, Journal of Power Sources, 155 (2006) 213-218.*

International Search Report and Written Opinion dated May 8, 2008; 12 pages.

Notification of Reason for Refusal dated Jul. 10, 2012 with English translation (four (4) pages).

Decision to Grant a Patent dated Dec. 11, 2012 w/ partial English translation(four (4) pages).

"HMI41 Indicator and HMP42/HMP46 Probes", Vaisala (Three (3) pages) (Copyright 2013).

"Vaisala HUMICAP Sensor for Measuring Relative Humidity", Vaisala/Technology Description (Two (2) pages) (Copyright 2012).

* cited by examiner

FUEL CELL SYSTEM WITH ULTRASONIC DETECTOR

This application is a national stage of International Application No. PCT/EP2008/000283, filed Jan. 16, 2008, which claims priority under 35 U.S.C. §119 to German Patent Application No. 10 2007 003 938.9, filed Jan. 26, 2007, the entire disclosure of which is herein expressly incorporated by reference.

BACKGROUND AND SUMMARY OF THE INVENTION

The present invention relates to a fuel cell system with fuel cells assembled in modular manner, and having at least one channel system for the inlet, circulation and outlet of fluid operating substances.

In order to achieve a high level of efficiency when generating power, devices are provided which control or adjust pressure, temperature, humidity and/or the composition of at least one operating substance. To detect the actual values of the variables to be controlled or adjusted, sensors are used which are preferably arranged on a storage tank, on a device for producing the substances to be reacted and/or on a channel of a channel system.

German patent document DE 100 47 248 A1 discloses a typical structure of a proton exchange membrane fuel cell system (PEM fuel cell system), with a cathode electrode, an anode electrode and a matrix, which together form a membrane electrode unit (MEA). Both the cathode electrode and the anode electrode have an electrically conductive body, which serves as a support for a catalyst material. The matrix is arranged between the cathode electrode and the anode electrode and serves as a support for an electrolyte.

A plurality of fuel cells are stacked on one another with interposed separator plates. The inlet, circulation and outlet of oxidants (oxidizing agents), reductants (fuel) and coolants proceed via channel systems, which are produced using the separator plates. For each liquid or gaseous operating medium, supply collector channels, distributor channels and outlet collector channels are provided in the fuel cell stack, separated from one another by sealing means. Via at least one inlet collector channel, the cells of a stack are supplied in parallel with an oxidant fluid, a reductant fluid and a coolant. The reaction products, excess reductant and oxidant fluid and heated coolant from the cells are fed out of the stack via at least one outlet collector channel. The distributor channels form a connection between the inlet and outlet collector channels and the individual active channels of a fuel cell. The fuel cells may be connected in series to increase voltage. The stacks are closed by end plates and accommodated in a housing, the positive and negative poles being conveyed outside to a consumer unit.

In a PEM fuel cell system, in which the fuel contains hydrogen, a gas mixture of air and water vapour is supplied on the cathode side. The dew point of the gas mixture should be approximately 5° C. below the gas temperature. To achieve this at any desired operating temperatures, a device may be provided for humidity control which has constant actual value determination.

It is known to use an optical or capacitive sensor to measure actual humidity. The reliability and measuring accuracy of these sensors is impaired, however, if a liquid film forms on a sensor surface.

It is also known to determine the actual humidity level indirectly, by measuring temperature and pressure. Such measuring instruments, however, are complex, and have a low dynamic range of measurement.

In German patent document DE 101 49 333 A1, the humidity of a gas is determined with a resistance measuring structure that cooperates with a layer of carbon black. The speed of measurement is low, though, and the resistance measuring structure can be used only in a narrow channel of a fuel cell system due to its structural size.

German patent document DE 199 44 047 A1 discloses a device for measuring the concentration or density and the velocity of particles in a flowing fluid. For this purpose, an ultrasonic detector is provided on a channel wall. The sound waves issuing from an ultrasonic transmitter in multifrequency operation are reflected by the particles, and the reflected waves are received by an ultrasonic receiver. The frequency shift and ultrasonic absorption brought about by the particle motion in accordance with the Doppler principle are evaluated. The particles detectable with the device range in size from 1 μm to 1000 μm.

In a cooking apparatus according to German patent document DE 101 43 841 A1, the density of a cooking atmosphere in a cooking chamber is determined by measuring sound velocity, in order to derive therefrom the content of water vapour and thus the humidity of the cooking atmosphere. In this application, account is taken of the fact that the cooking temperature influences the density of the cooking atmosphere. Sound velocity measurement may be performed in a measuring tube, which is connected atmospherically to the cooking chamber. Sound velocity is measured using an ultrasonic transmitter and an ultrasonic receiver, (which may be combined into a single unit), with a known measurement path therebetween.

One object of the present invention is to provide a fuel cell system which includes a device for adjusting the moisture content of the working fluid flowing in one direction in a channel system, and which allows reliable and dynamic measurement of the actual humidity.

This and other objects and advantages are achieved by the fuel cell system according to the invention, which uses an ultrasonic detector to measure the actual humidity. The invention is particularly advantageously applicable to the measurement of the actual humidity on the cathode side of a fuel cell system.

To measure actual humidity, sound velocity is preferably determined in a working fluid flowing in a channel of a channel system, from which a dew point temperature is derived. The ultrasonic detector comprises a transmitter and a receiver, which are arranged at a known distance from one another. At identical temperature, sound velocity in water vapour is higher than in dry air. This means that as the humidity of the working fluid rises, sound velocity increases along the measurement path. Since the vapour pressure of water increases exponentially as the temperature rises, the accuracy of the measurement principle increases on the one hand as the temperature increases, and on the other hand, as the respective dew point of the working fluid is approached.

Other objects, advantages and novel features of the present invention will become apparent from the following detailed description of the invention when considered in conjunction with the accompanying drawings.

DETAILED DESCRIPTION OF THE DRAWINGS

Figure 1:
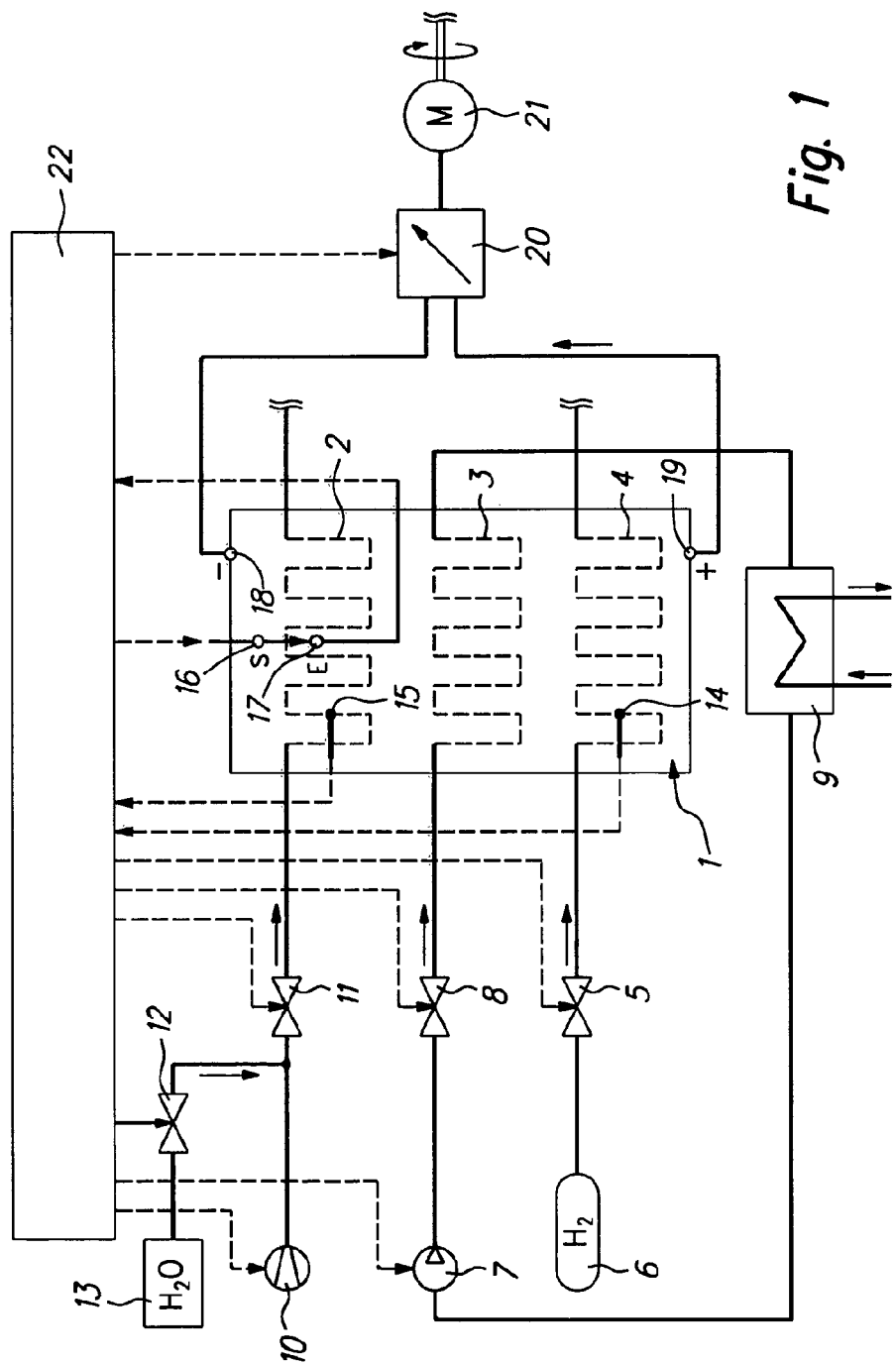
FIG. 1 is a diagram of a fuel cell system according to the invention, with a device for adjusting the humidity in a cathode channel system.

FIG. 1 is a diagram of a fuel cell system 1 with a device for adjusting the humidity in a cathode channel system 2. In addition to the cathode channel system 2, the fuel cell system 1 comprises a cooling channel system 3 and an anode channel system 4. Hydrogen is supplied to the anode channel system 4 from a high pressure hydrogen tank 6 via a controllable valve 5. Cooling water flows through the cooling channel system 3 in a circuit having a pump 7, a controllable valve 8 and a heat exchanger 9. Oxygen-containing air is supplied to the cathode channel system 2 using a blower 10 via a controllable valve 11. Water vapour from a water vapour generator 13 is added to the air via a controllable valve 12. Temperature sensors 14, 15 are arranged in the anode channel system 4 and the cathode channel system 2.

An ultrasonic detector associated with the cathode channel system 2 comprises an ultrasonic transmitter 16 and an ultrasonic receiver 17. The cathode electrode 18 and the anode electrode 19 are connected to a current controller 20. An electric motor 21 of a motor vehicle is connected to the current controller 20. The pump 7, the blower 10, the valves 5, 8, 11, 12, the temperature sensors 14, 15, the transmitter 16, the receiver 17 and the current controller 20 are connected to a control and adjustment device 22.

During operation of the fuel cell system 1, the humidity of the air in the cathode channel system 2 is measured constantly using the transmitter 16 and receiver 17. Ultrasonic waves issued from the transmitter 16 penetrate the moist air in the cathode channel system 2 and impinge on the receiver 17. The transmitter 16 and the receiver 17 are at a known distance from one another, so that, based on the propagation time of the sound waves and the distance between transmitter 16 and receiver 17, a sound velocity can be calculated, which is dependent on the current humidity of the air.

The actual humidity, determined from the signals of the receiver 17 in the control device 22, is then compared with a stored reference humidity, the difference between actual and reference values is compensated by opening or closing the valve 12 to a greater or lesser extent using the control device 22. In this way, more or less water vapour from the water vapour generator 13 is fed into the air conveyed with the blower 10. When determining the control variables for the valve 12, the temperature in the cathode channel system 2 is taken into account. This temperature is obtained from the measured values of the temperature sensor 15.

Figure 2:
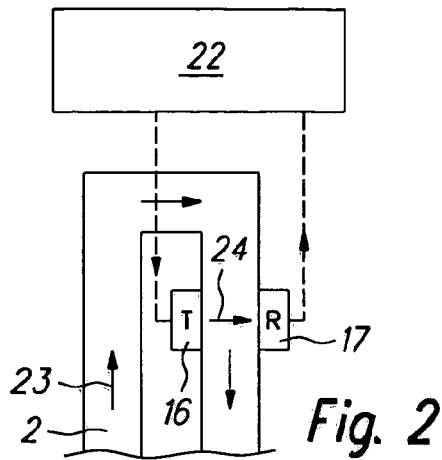
FIG. 2 shows an ultrasonic detector, with a transmitter and a receiver situated transversely of the direction of flow of an air/water vapour mixture.
Figure 3:
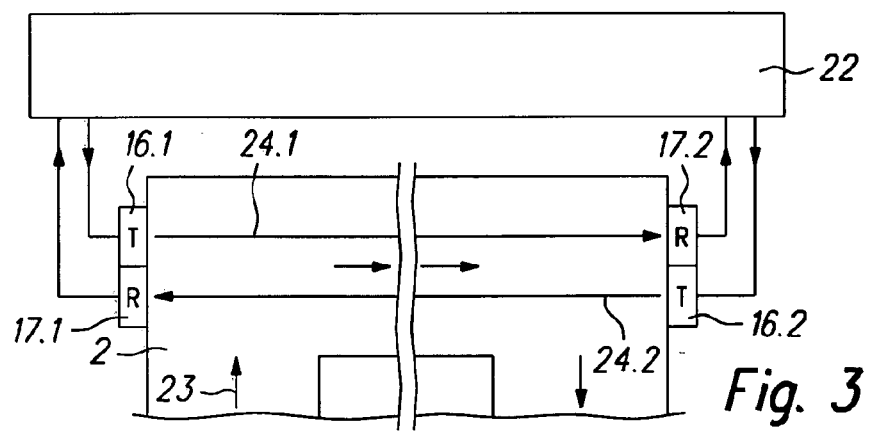
FIG. 3 shows an ultrasonic detector with a transmitter and a receiver arranged in the direction of flow of an air/water vapour mixture.
Figure 4:
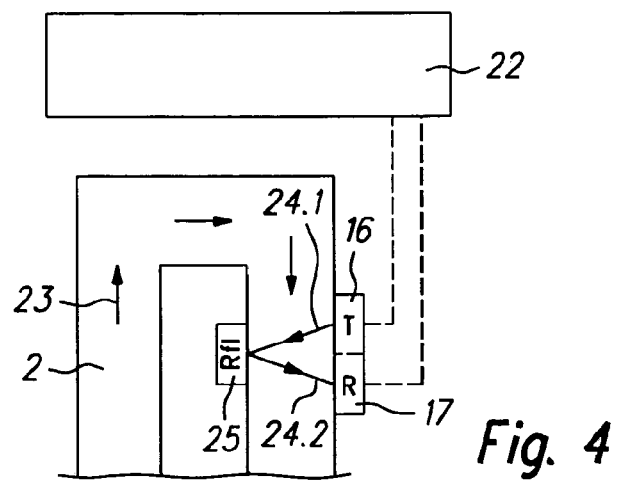
FIG. 4 shows an ultrasonic detector arranged together with transmitter and receiver in a housing.

FIGS. 2-4 illustrate variants of an arrangement for transmitter 16 and receiver 17 in the cathode channel system 2.

In the variant according to FIG. 2, the moist, oxygen-containing air flows through the cathode channel system 2 in the direction of the arrow 23, and the transmitter 16 and the receiver 17 are arranged in an area of the cathode channel system 2 in which the air flows in a laminar manner, in such a way that the ultrasonic waves 24 run transversely of the direction of flow 23.

In FIG. 3 on the other hand, two pairs of transmitters 16.1, 16.2 and receivers 17.1 and 17.2 are provided in a portion of the cathode channel system 2 with laminar flow. The ultrasonic waves 24.1, 24.2 issuing from the transmitter 16.1, 16.2 run with and against the direction of flow 23 of the cathode gas mixture. To avoid measurement errors when measuring humidity, the sound velocities with and against the direction of flow 23 of the air/water vapour mixture are determined from the signals from the receivers 17.1, 17.2. The difference between the two sound velocity signals may also be used to determine the flow rate of the mixture.

FIG. 4 shows a variant in which an ultrasonic transmitter 16 and an ultrasonic receiver 17 are arranged in a common housing on one side of a cathode channel 2. Measurement of the sound velocity or the humidity of an air/water vapour mixture is independent of the direction of flow 23. As a result of arrangement in the common housing, the ultrasonic detector is cheap to manufacture and mount, and takes up only a small amount of structural volume. The wall of the cathode channel 2 facing the transmitter 16 and the receiver 17 takes the form of an ultrasonic reflector 25. Ultrasonic waves 24.1 issue from the transmitter 16 and impinge on the reflector 25. The waves 24.2 reflected back from the reflector 25 are received by the receiver 17.

Figure 5:
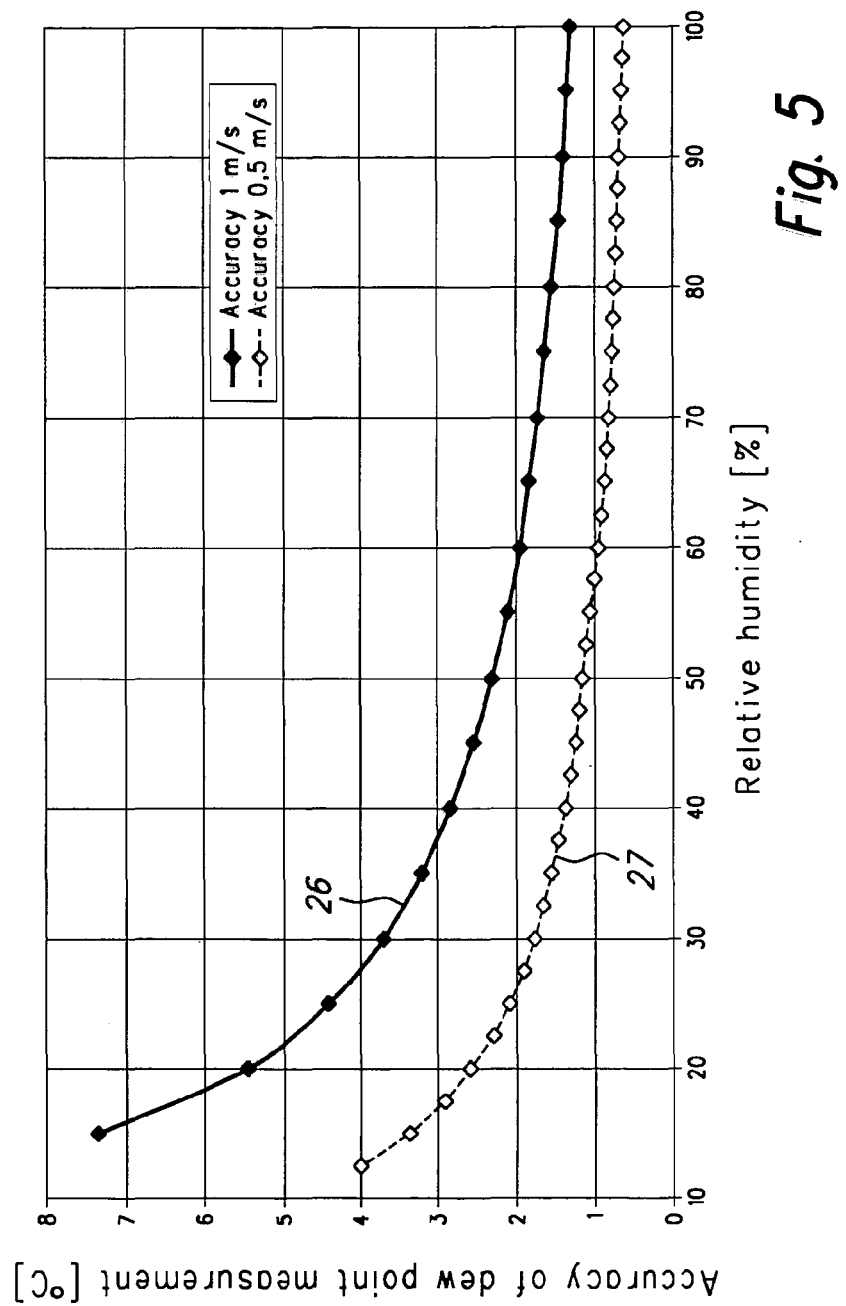
FIG. 5 is a diagram showing the accuracy of humidity measurement.

The diagram illustrated in FIG. 5 shows a dependent relationship between accuracy when determining a dew point temperature and the relative humidity in a working fluid of a fuel cell system at a working fluid temperature of 80° C. and an absolute pressure of 2.2 bar. The curves 26, 27 are obtained from different accuracies when measuring the sound velocity in the working fluid with an ultrasonic detector. As described above, measured humidity values are derived from the measured sound velocity values. The curve 26 results from a measuring accuracy of 1 m/s. The curve 27 applies to a measuring accuracy of 0.5 m/s. It is clear from curve 27 that, at a relative humidity level of between 60% and 100%, the error when determining the dew point temperature is below 1° C. It is thus possible in each case to ensure, by humidity adjustment, that the dew point of the working fluid is always below the working fluid temperature by a predetermined amount, of for example 5° C.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

LIST OF REFERENCE NUMERALS USED

1 Fuel cell system
2 Cathode channel system
3 Cooling channel system
4 Anode channel system
5 Valve
6 High pressure hydrogen tank
7 Pump
8 Valve
9 Heat exchanger
10 Blower
11, 12 Valve
13 Water vapour generator
14, 15 Temperature sensor
16 Ultrasonic transmitter
17 Ultrasonic receiver
18 Cathode electrode 19 Anode electrode
20 Current controller
21 Electric motor
22 Control and adjustment device
13 Arrow
24 Ultrasonic wave
25 Ultrasonic reflector
26, 27 Curve

The invention claimed is:

1. A fuel cell system comprising:
a plurality of fuel cells stacked on one another with interposed separator plates, the interposed separator plates forming at least one cathode channel system for a working fluid;
a device configured to adjust the humidity content of the working fluid flowing in one direction in the cathode channel system; and
a sensor configured to directly measure actual humidity in the cathode channel system;
wherein the sensor comprises an ultrasonic detector arranged within the separator plates so that only a face of the ultrasonic detector is exposed to the working fluid within the cathode channel system.

2. The fuel cell system according to claim 1, wherein the ultrasonic detector comprises:
an ultrasonic transmitter with a main transmitting direction; and
an ultrasonic receiver with a main receiving direction;
wherein the main transmitting and main receiving directions lie transversely to a direction of flow of the working fluid.

3. The fuel cell system according to claim 1, wherein the ultrasonic detector comprises:
an ultrasonic transmitter with a main transmitting direction; and
an ultrasonic receiver with a main receiving direction;
where the main transmitting and main receiving directions lie in a direction of flow of the working fluid.

4. The fuel cell system according to claim 3, wherein two ultrasonic detectors are provided with opposed transmitting and receiving directions.

5. A fuel cell system comprising:
a plurality of fuel cells stacked on one another with interposed separator plates, the interposed separator plates forming at least one cathode channel system for a working fluid;
a device configured to adjust the humidity content of the working fluid flowing in one direction in the cathode channel system; and
an ultrasonic detector configured to directly measure actual humidity in the cathode channel system,
wherein the ultrasonic detector comprises an ultrasonic transmitter and an ultrasonic receiver which are arranged in a common housing, and which are arranged in the fuel cell system in such a manner that the measurement of actual humidity is independent of a direction of flow of the working fluid through the cathode channel system.

6. The fuel cell system according to claim 5, wherein an ultrasonic reflector is provided on an opposite wall of the cathode channel system and at a predetermined distance from the transmitter and the receiver.

7. A method for a fuel cell system comprising:
directly measuring, by an ultrasonic detector, actual humidity in a cathode channel system for a working fluid, wherein the cathode channel system is formed by interposed separator plates of a plurality of fuel cells stacked on one another; and
adjusting, by a device, the humidity content of the working fluid flowing in one direction in the cathode channel system,
wherein the ultrasonic detector is arranged within the separator plates so that only a face of the ultrasonic detector is exposed to the working fluid within the cathode channel system.

8. The method according to claim 7, wherein the ultrasonic detector directly measures the actual humidity in the cathode channel system by:
transmitting, by an ultrasonic transmitter of the ultrasonic detector, in a main transmitting direction; and
receiving, by an ultrasonic receiver of the ultrasonic detector, the transmission from the ultrasonic transmitter in a main receiving direction;
wherein the main transmitting and main receiving directions lie transversely to a direction of flow of the working fluid.

9. The method according to claim 7, wherein the ultrasonic detector directly measures the actual humidity in the cathode channel system by:
transmitting, by an ultrasonic transmitter of the ultrasonic detector, in a main transmitting direction; and
receiving, by an ultrasonic receiver of the ultrasonic detector, the transmission from the ultrasonic transmitter in a main receiving direction;
wherein the main transmitting and main receiving directions lie in a direction of flow of the working fluid.

10. The fuel cell system according to claim 1, further comprising:
a temperature sensor arranged in the cathode channel system, the temperature sensor is arranged to directly measure an actual temperature in the cathode channel system,
wherein the device configured to adjust the humidity content of the working fluid is configured to adjust the humidity content based on the measured actual humidity and temperature in the cathode channel system, and
wherein the temperature sensor and ultrasonic detector are separate sensors.

11. The method according to claim 7, further comprising:
directly measuring, by a temperature sensor arranged in the cathode channel system, an actual temperature in the cathode channel system,
wherein the adjustment of the humidity content of the working fluid adjusts the humidity content based on the measured actual humidity and temperature in the cathode channel system, and
wherein the temperature sensor and ultrasonic detector are separate sensors.

* * * * *